United States Patent
Lubner et al.

(10) Patent No.: US 9,851,316 B2
(45) Date of Patent: Dec. 26, 2017

(54) SYSTEM AND METHOD FOR DETERMINING A SPATIAL THERMAL PROPERTY PROFILE OF A SAMPLE

(71) Applicants: Sean D. Lubner, Berkeley, CA (US); Jeunghwan Choi, Roseville, MN (US); Harishankar Natesan, Minneapolis, MN (US); Christopher E. Dames, Granada Hills, CA (US); John C. Bischof, St. Paul, MN (US)

(72) Inventors: Sean D. Lubner, Berkeley, CA (US); Jeunghwan Choi, Roseville, MN (US); Harishankar Natesan, Minneapolis, MN (US); Christopher E. Dames, Granada Hills, CA (US); John C. Bischof, St. Paul, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 505 days.

(21) Appl. No.: 14/533,510

(22) Filed: Nov. 5, 2014

(65) Prior Publication Data

US 2015/0127294 A1 May 7, 2015

Related U.S. Application Data

(60) Provisional application No. 61/901,132, filed on Nov. 7, 2013.

(51) Int. Cl.
*G01N 25/18* (2006.01)
*A61B 5/01* (2006.01)
(Continued)

(52) U.S. Cl.
CPC ............ *G01N 25/18* (2013.01); *A61B 5/01* (2013.01); *A61B 5/053* (2013.01); *A61B 18/02* (2013.01);
(Continued)

(58) Field of Classification Search
CPC ..................................................... G01N 25/18
See application file for complete search history.

(56) References Cited

FOREIGN PATENT DOCUMENTS

CN 101975794 A 2/2011

OTHER PUBLICATIONS

Duquesne et al., Analytical Solutions of the heat diffusion equation for 3w method geometry, Journal of APplied Physics, 108, 096104, (2010), 3pgs.*

(Continued)

*Primary Examiner* — Phuong Huynh
(74) *Attorney, Agent, or Firm* — Schwegman Lundberg & Woessner, P.A.

(57) ABSTRACT

A sensing system uses three-omega sensing to determine a spatial profile of thermal property within a sample. The sensing system electrically powers a lossy electrical conductor at different driving frequencies. The different driving frequencies produce different penetration depths within the sample. The sensing system takes multiple measurements of thermal property at the different driving frequencies. Each measurement is associated with a different penetration depth, and therefore is averaged over a differently-sized volume within the sample. The sensing system performs a fit on the multiple measurements of material thermal property versus material geometry. If one of thermal property or geometry is known beforehand, then the fit can determine the other. The lossy electrical conductor can be formed on a polymeric flexible membrane, on a probe that can be placed at a suitable location in a patient's body, and/or directly onto a heating or cooling element.

15 Claims, 12 Drawing Sheets

(51) Int. Cl.
| | |
|---|---|
| A61B 5/053 | (2006.01) |
| G06F 11/30 | (2006.01) |
| A61B 18/02 | (2006.01) |
| A61B 18/00 | (2006.01) |

(52) U.S. Cl.
  CPC ............... *A61B 2018/00708* (2013.01); *A61B 2018/00791* (2013.01); *A61B 2018/00875* (2013.01)

(56) References Cited

OTHER PUBLICATIONS

Albage, A., et al., "Learning what works in surgical cryoablation of atrial fibrillation: results of different application techniquess and benefits of prospective follow-up", *Interactive CardioVascular and Thoracic Surgery*, 13, (2011), 480-484.

Bahn, D. K., et al., "Targeted Cryoablation Treatment of Prostate: 7-Year Outcomes in the Primary Treatment of Prostate Cancer", *Urology*, 60 (Suppl. 2A), (Aug. 2002), 3-11.

Balasubramaniam, T. A., et al., "Thermal Conductivity and Thermal Diffusivity of Biomaterials: A Simultaneous Measurement Technique", *Journal of Biomechanical Engineering*, 99(3), (Aug. 1977), 148-154.

Bischof, J., et al., "A Morphological Study of Cooling Rate Response in Normal and Neoplastic Human Liver Tissue: Cryosurgical Implications", *Cryobiology*, 30, (1993), 482-492.

Bowman, H. F., et al., "Theory, Measurement, and Application of Thermal Properties of Biomaterials", *Annu. Rev. Biophys. Bioeng.*, 4, (1975), 43-80.

Cahill, D. G., "Thermal conductivity measurement from 30 to 750 K: the 3ω method", *Rev. Sci. Instrum.*, 61(2), (Feb. 1990), 802-808.

Cahill, D. G., et al., "Thermal conductivity of α-Si:H thin films", *Physical Review B*, 50(9), (1994), 6077-6081.

Chen, F., et al., "Thermal conductivity measurement under hydrostatic pressure using the 3ω method", *Review of Scientific Instruments*, 75(11), (Nov. 2004), 4578-4584.

Choi, J. H., et al., "A quantitative analysis of the thermal properties of porcine liver", *Cryobiology*, 57, (2008), 79-83.

Choi, J., et al., "Review of biomaterial thermal property measurement in the cryogenic regime and their use for prediction of equilibrium and non-equilibrium freezing applications in cryobiology", *Cryobiology*, 60, (2010), 52-70.

Choi, J., et al., "Thermal Processing of Biological Tisse at High Temperatures: Impact of Protein Denaturation and Water Loss on the Thermal Properties of Human and Porcine Liver in the Range 25-80° C.", *Journal of Heat Transfer*, vol. 135, (2013), 7 pgs.

Cooper, T. E., et al., "A Probe Technique Determining the Thermal Conductivity of Tissue". *Journal of Heat Transfer*, 94(2), (May 1972), 133-140.

Dames, C., et al., "1ω, 2ω, and 3ω methods for measurements of thermal properties", *Review of Scientific Instruments*, 76, 124902, (2005), 14 pgs.

Davol, P. E., et al., "Long-Term Results of Cryoablation for Renal Cancer and Complex Renal Issues", *Urology*, 68 (Suppl. 1A), (Jul. 2006), 2-6.

Diaz, M. L., et al., "Cryoplasty Versus Conventional Angioplasty in Femoropopliteal Arterial Recanalization: 3-Year Analysis of Reintervention-Free Survival by Treatment Received", *Cardiovasc Intervent Radiol*, 34, (2011), 911-917.

Duquesne, J.-Y., et al., "Analytical solutions of the heat diffusion equation for 3ω method geometry", *Journal of Applied Physics*, 108, 086104, (2010), 3 pgs.

Fahy, G. M., "Cryopreservation of Complex Systems: The Missing Link in the Regenerative Medicine Supply Chain", *Rejuvenation Research*, 9(2), (2006), 279-291.

Ge, Z., et al., "Thermal Conductance of Hydrophilic and Hydrophobic Interfaces", *Physical Review Letters*, 96, 186101, (2006), 4 pgs.

Geidel, S., et al., "Ablation surgery in patients with persistent atrial fibrillation: An 8-year clinical experience", *The Journal of Thoracic and Cardiovascular Surgery*, 141(12), (Feb. 2011), 377-382.

Lencioni, R. A., et al., "Small Hepatocellular Carcinoma in Cirrhosis: Randomized Comparison of Radio-frequency Thermal Ablation versus Percutaneous Ethanol Injection", *Radiology*, 228(1), (Jul. 2003), 235-240.

Lubner, S. D., et al., "Measurements of the Thermal Conductivity of Sub-Millimeter Biological Tissues", *Proceedings of the ASME 2012 International Mechanical Engineering Congress & Exposition (IMECE 2012)*, Nov. 9-15, 2012, Houston, TX, (2012), 1-8.

Lubner, S. D., et al., "Reusable Bi-Directional 3ω Sensor to Measure Thermal Conductivity of 100-micron Thick Biological Tissues", 1-24.

Moon, I. K., et al., "The 3 technique for measuring dynamic specific heat and thermal conductivity of a liquid or solid", *Rev. Sci. Instrum.*, 67(1), (Jan. 1996), 29-35.

Murad, S., et al., "Thermal transport through a fluid-solid interface", *Chemical Physics Letters*, (2009), 267-270.

Natesan, H., et al., "In-vivo Thermal Monitoring of Cryoablation of Pulmonary Vein Using a 3 Omega Thermal Sensor", Poster CE10, *The Annual Conference and Retreat, Institute for Engineering in Medicine*, (Sep. 22, 2014), 1 pg.

Oh, D.-W., et al., "Thermal conductivity measurement and sedimentation detection of aluminum oxide nanofluids by using the 3ω method", *International Journal of Heat and Fluid Flow*, 29, (2008), 1456-1461.

Rossi, S., et al., "Percutaneous RF Interstitial Thermal Ablation in the Treatment of Hepatic Cancer", *AJR Am J Roentgenol*, 167(3), (Sep. 1996), 759-768.

Sabel, M. S., et al., "Cryoablation of Early-Stage Breast Cancer: Work-in-Progress Report of a Multi-Institutional Trial", *Annals of Surgical Oncology*, 11(5), (2004), 542-549.

Sobotka, P. A., et al., "Sympatho-renal axis in chronic disease", *Clin Res Cardiol*, 100, (2011), 1049-1057.

Song, Y. C., et al., "Vitreous cryopreservation maintains the function of vascular grafts", *Nature Biotechnology*, 18, (Mar. 2000), 296-299.

Tong, T., et al., "Reexamining the 3-omega technique for thin film thermal characterization", *Review of Scientific Instruments*, 77, 104902, (2006), 9 pgs.

Valvano, J. W., "Chapter 12—Tissue Thermal Properties", *In: Optical-Thermal Response of Laser-Irradiated Tissue*, 2nd Edition, A. J. Welch, et al., Editors, Springer Science+Business Media B.V., (2011), 455-485.

Yamane, T., et al., "Measurement of thermal conductivity of silicon dioxide thin films using a 3ω method", Measurement of thermal conductivity of silicon dioxide thin films using a 3ω method, *Journal of Applied Physics*, 91(12), (2002), 9772-9776.

Yang, J.-H., et al., "Midterm Results of Size-Reduced Cryopreserved Homografts for Right Ventricular Outflow Tract Reconstruction", *Ann. Thorac. Surg.*, 89, (2010), 1821-1826.

Zhang, H., et al., "Determination of Thermal Conductivity of Biomaterials in the Temperature Range 233-313° K Using a Tiny Detector Made of a Self-Heated Thermistor", *Cell Preservation Technology*, 1(2), (2002), 141-147.

\* cited by examiner

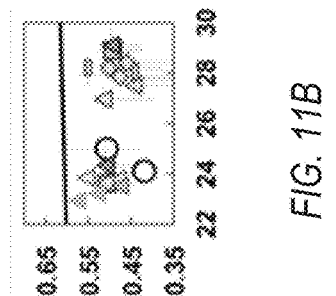
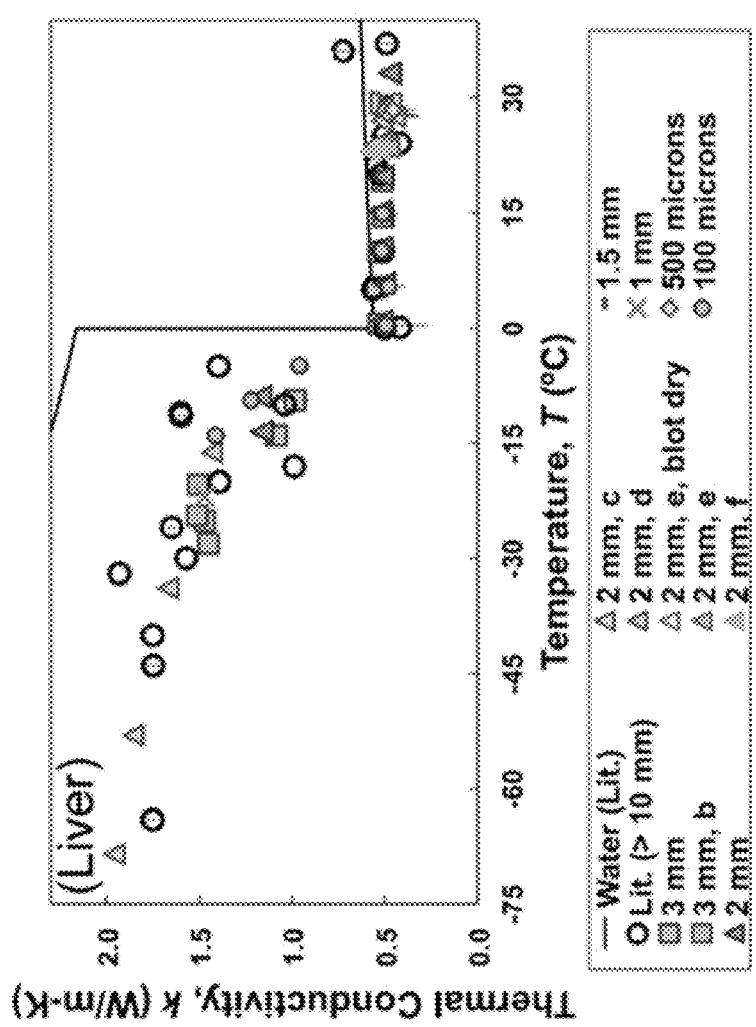
FIG. 11B
FIG. 11A

SYSTEM AND METHOD FOR DETERMINING A SPATIAL THERMAL PROPERTY PROFILE OF A SAMPLE

CROSS REFERENCE TO RELATED APPLICATION

This application claims the benefit of U.S. Provisional Application No. 61/901,132, filed Nov. 7, 2013, which is incorporated by reference herein in its entirety.

STATEMENT REGARDING FEDERALLY SPONSORED RESEARCH OR DEVELOPMENT

This invention was made with government support under CBET-1236760 awarded by the National Science Foundation. The government has certain rights in the invention.

THE NAMES OF THE PARTIES TO A JOINT RESEARCH AGREEMENT

This invention was made under a joint research agreement between The Regents of the University of Minnesota and The Regents of the University of California, Berkeley.

BACKGROUND

In the field of cryosurgery, a practitioner freezes diseased or unwanted tissue to destroy the tissue. Cryosurgery has been used for treatment throughout the human body, including cancer treatment, cardiovascular applications, and neural applications, among others.

In one example from the 1980s, practitioners used cryosurgery to treat liver cancer. During the treatment, a practitioner formed relatively large iceballs that were larger than the cancer by 1 cm or more, which created a surgical margin around the cancer. In order to prevent unwanted damage to surrounding tissue, the practitioner used typical clinical imaging technology to monitor the size and location of the iceballs, such as ultrasound (US), magnetic resonance imaging (MRI) and computed tomography (CT). For the relatively large iceballs used for liver cancer treatment in the 1980s, the typical clinical imaging technology was sufficient to monitor the iceball size and location.

Over time, practitioners have used cryosurgery to treat increasingly more intricate areas of the body, which include relatively fine tissue and structures. Treatment of these intricate areas requires increasingly precise monitoring of the size and location of the iceballs, in order to prevent damage to surrounding tissue and organs. For instance, during treatment of the prostate for prostate cancer, a practitioner carefully avoids damaging the rectum, bladder, and neurovascular bundle, which are all located within a few mm of the prostate. Imprecise monitoring of the iceball size and location during prostate treatment can damage these adjacent organs, and can lead to complications, such as fistulas, incontinence, and impotence. As another example, during treatment of atrial fibrillation, a practitioner uses a cryoballoon in the pulmonary vein to form a 2 mm-thick iceball throughout the vein wall. During the procedure, the practitioner carefully avoids freezing adjacent tissue, such as the lung, esophagus, and phrenic nerve.

In general, the typical clinical imaging technologies of ultrasound, magnetic resonance, and computed tomography do not have a resolution fine enough to accurately monitor iceball formation in the more intricate areas of the body. Accordingly, there exists a need for a monitoring system and method that can monitor an edge of a frozen region with sufficient precision to be used for the relatively thin tissues in the more intricate parts of the human body. Such a monitoring system and method could have other applications, such as monitoring heat-based elements.

OVERVIEW

A sensing system uses three-omega sensing to determine a spatial profile of thermal property within a sample. The sensing system electrically powers a lossy electrical conductor at different driving frequencies. The sensing system can power the different frequencies sequentially, or can power two or more different frequencies simultaneously. The different driving frequencies produce different penetration depths within the sample. The sensing system takes multiple measurements of thermal property at the different driving frequencies. Each measurement is associated with a different penetration depth, and therefore is averaged over a differently-sized volume within the sample. The sensing system performs a fit on the multiple measurements of material thermal property versus material geometry. If one of thermal property or geometry is known beforehand, then the fit can determine the other. The lossy electrical conductor can be formed on a polymeric flexible membrane, on a probe that can be placed at a suitable location in a patient's body, and/or directly onto a heating or cooling element. In some examples, the sensing system can use multiple sensors to determine a two- or three-dimensional representation of the thermal property.

The thermal property being detected can be thermal conductivity, thermal diffusivity, volumetric heat capacity, or thermal effusivity, or any combination thereof. In general, these four quantities are interrelated, so that any two of the quantities can be calculated from the other two quantities.

One example of a suitable application for the sensing system and method described herein is monitoring an edge of a frozen region during cryosurgery. For instance, the lossy electrical conductor can be disposed on a cryoballoon, and the sensing system and method can provide dynamic readings of iceball size created by the cryoballoon. For this example, the thermal property values of frozen and un-frozen tissue are different from each other and are generally well-known, while the geometry of the frozen and un-frozen tissues are to be determined. The sensing system takes multiple measurements, each at a different driving frequency, and, therefore, each with a different penetration depth into the sample. The sensing system performs a fit of the multiple measurements, and can solve for a geometry of the frozen and un-frozen tissue. The geometry indicates a location of a boundary between frozen tissue and un-frozen tissue, which is indicative of a size of an iceball. The sensing system provides this information to a practitioner in real time or nearly real-time, which can help prevent damage to tissue surrounding the surgical location.

Another example of a suitable application for the sensing system and method described herein is detecting an edge of a tissue boundary. For instance, a boundary can occur between different tissue types, which have different thermal properties. Such different tissue types include lipid, fatty, protein, fibrous, cellular, and others. In some examples, the sensing system can have resolutions smaller than those currently available from typical clinical imaging techniques. In some examples, the sensing system and method can form a two-dimensional or a three-dimensional map of the tissue. In some examples, the maps can provide more accurate geometry data than typical clinical imaging techniques.

Another example of a suitable application for the sensing system and method described herein is dynamically tracking a thermal phase front as it moves through tissue, which can provide temporal information about the thermal phase front. For instance, as a cooling element begins freezing surrounding tissue, an iceball begins growing through the surrounding tissue. The edge of the iceball is a boundary between frozen and un-frozen tissue. The boundary can grow, shrink or otherwise move over time, so that sensing system and method can track the boundary over time. The sensing system can take repeated measurements over time of a thermal spatial profile, which can provide evolutionary information about thermal phase front. This tracking information can be used during treatment of a patient, in order to avoid freezing healthy tissue. For instance, the sensing system can track a thermal phase front as it approaches a boundary between different tissue types. A practitioner using the sensed information can allow the thermal phase front to pass through the boundary, or can takes suitable steps to ensure that the thermal phase front does not cross the boundary. In some examples, the tracking information can be used when developing procedures for treatment, such as determining suitable times or power levels for a particular procedure. These are but three examples of applications for the sensing system and method described herein. Other uses are also possible.

Another example of a suitable application for the sensing system and method described herein is sensing a heating front where water loss and protein denaturation occur.

Additional examples of suitable applications for the sensing system and method described herein are heat-based focal therapies and irreversible electroporation. In some of these therapies, there can be an intention to treat to the margin of a tumor, but a desire to avoid excessive treatment and collateral injury beyond the tumor.

In some examples, using the sensing system and method described herein can resolve a thickness and/or a geometry of features that can be too small to resolve using typical clinical imaging. In some examples, using the sensing system and method described herein can resolve both static features and time-varying features that can evolve during a procedure.

This Overview is intended to provide examples of subject matter of the present patent document. It is not intended to provide an exclusive or exhaustive explanation of the invention. The Detailed Description below is included to provide further information about the present modular hip stems and the corresponding methods.

BRIEF DESCRIPTION OF THE DRAWINGS

In the drawings, which are not necessarily drawn to scale, like numerals can describe similar components in different views. The drawings illustrate generally, by way of example, but not by way of limitation, various embodiments discussed in the present patent document.

FIG. 11A shows thermal conductivity versus temperature for mouse liver.

FIG. 11B shows a close-up of data points from FIG. 11A.

DETAILED DESCRIPTION

Figure 1:
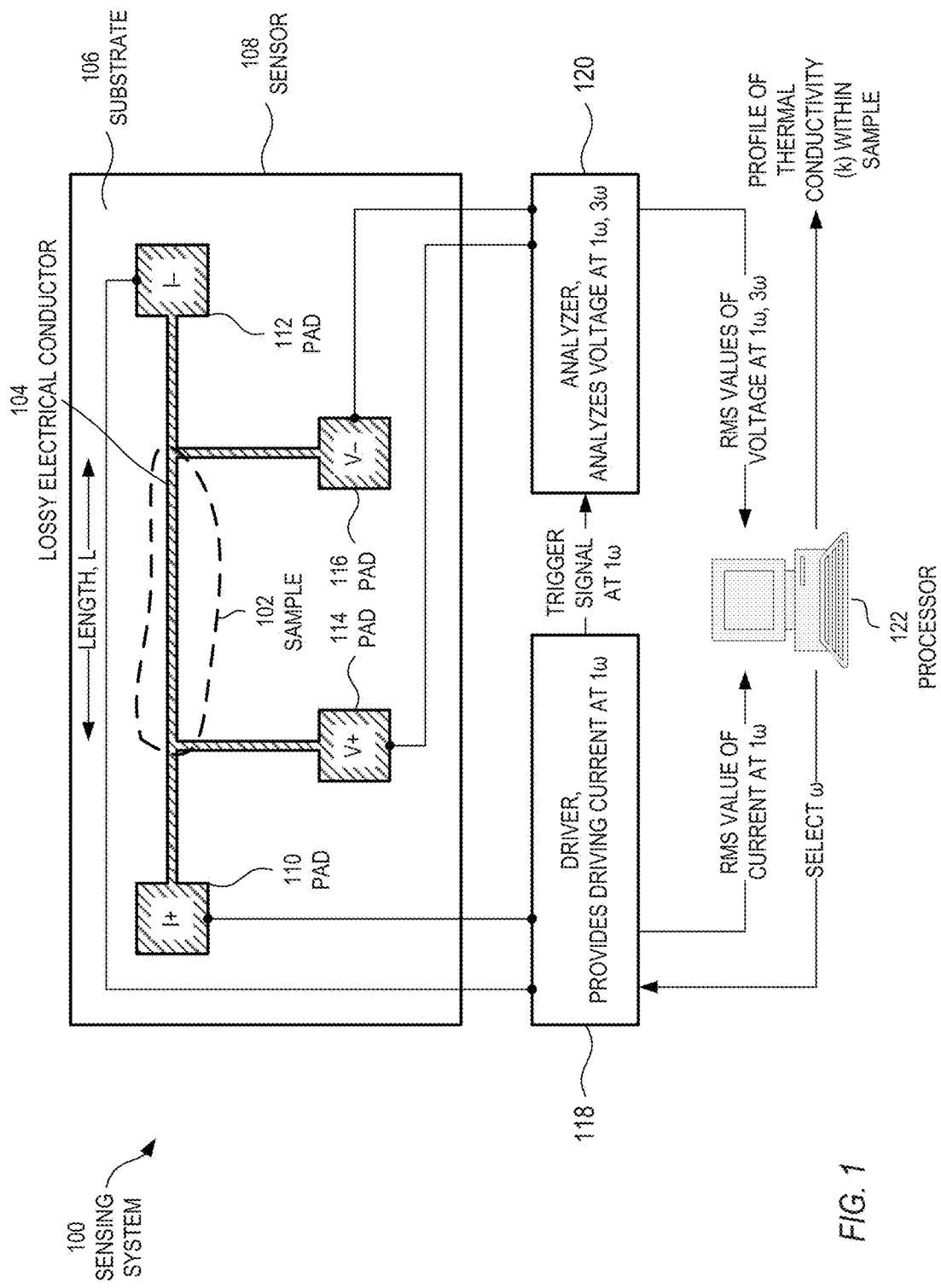
FIG. 1 is a schematic drawing of an example of a sensing system.

FIG. 1 is a schematic drawing of an example of a sensing system 100. The sensing system 100 can determine a thermal property of a sample 102. The sample 102 is not part of the sensing system 100.

The sensing system 100 includes a lossy electrical conductor 104 configured to thermally contact the sample 102. As used herein, the term lossy denotes that the electrical conductor has a resistance value suitable for producing heat when current is passed through the electrical conductor; this is commonly referred to as resistive heating. The lossy electrical conductor 104 can extend longitudinally over a length, L. The lossy electrical conductor 104 can have a uniform cross-section along its length. The lossy electrical conductor 104 can be configured to contact the sample 102 along length L, and can extend longitudinally beyond length L. In the example of FIG. 1, length L is the length along the lossy electrical conductor 104 over which current flows during operation; the length L in FIG. 1 is set by the spacing between pads 110, 112.

In some examples, the lossy electrical conductor 104 can be formed as a metallic layer, deposited on a substrate 106. To take a measurement, a practitioner can place the substrate 106 into contact with the sample 102, pass current through the lossy electrical conductor 104 to controllably radiate heat into the sample 102, measure a voltage across the lossy electrical conductor 104, and determine from the measured voltage thermal conductivity information about the sample. In some examples, the substrate 106 is electrically insulating, so that current flowing through the lossy electrical conductor 104 is not diverted into the substrate 106. In some examples, the substrate 106 can be a polymeric flexible membrane. In some examples, the substrate 106 can be a heating or cooling element, such as a cryoballoon. In some examples, the lossy electrical conductor 104 and the substrate 106 form a sensor 108. The sensor 108 can have any suitable shape. For instance, the sensor 108 can be formed as a probe, which can be placed at a suitable location in a patient's body. In some examples, a probe can be formed as an elongated element, with the substrate at a distal end and a handle at a proximal end, so that a practitioner can position or reposition the probe as need during a procedure.

The lossy electrical conductor 104 can be electrically coupled to contact pads 110, 112 at its longitudinal ends, and contact pads 114, 116 disposed at the longitudinal ends of the length L. One set of contact pads, such as 110, 112, can be used to electrically power the lossy electrical conductor 104. The other set of pads, such as 114, 116, can be used to measure voltage across the lossy electrical conductor 104. In general, either pair of pads, or any combination of pads, may be used for either powering or monitoring.

There are techniques that can calculate thermal property from the current flowing through the lossy electrical conductor 104 and the voltage across the lossy electrical conductor 104. One known technique is known as three-omega, or 3ω. The section titled "Three-omega method" provides additional details regarding three-omega sensing. In three-omega sensing, the lossy electrical conductor 104 is driven with an AC electrical signal at a driving frequency (ω), and the thermal property of material surrounding the lossy electrical conductor 104 can be calculated from a current value ($I_{1\omega,rms}$) at the driving frequency, a fundamental voltage value ($V_{1\omega,rms}$) at the driving frequency, and a third harmonic voltage value ($V_{3\omega,rms}$) at a third order harmonic of the driving frequency. Other calculation techniques can also be used.

A driver 118 is configured to electrically power the lossy electrical conductor 104 through pads 110, 112 at a selectable driving frequency (ω). The electrically powered lossy electrical conductor 104 carries a current therethrough. The current has a current value ($I_{1\omega,rms}$) at the selectable driving frequency. The current value can be expressed in terms of root-mean-square (RMS), peak, or another suitable metric. The driver 118 can provide the current value ($I_{1\omega,rms}$) as needed.

An analyzer 120 is configured to measure a voltage across the lossy electrical conductor 104 through pads 114, 116. The analyzer extracts from the measured voltage a fundamental voltage value ($V_{1\omega,rms}$) at the selectable driving frequency and a third harmonic voltage value ($V_{3\omega,rms}$) at a third order harmonic of the selectable driving frequency. In some examples, the analyzer 120 includes at least one lock-in amplifier. In some examples, the driver 118 provides a trigger signal to the analyzer 120 at the driving frequency (ω). In some examples, the analyzer 120 can include one or more spectrum analyzers, such as a Fast Fourier Transform (FFT) module. When a Fast Fourier Transform is used, the trigger signal can be omitted. The analyzer 120 can provide the fundamental voltage value ($V_{1\omega,rms}$) and the third harmonic voltage value ($V_{3\omega,rms}$), as needed.

A processor 122 is coupled to the driver 118 and the analyzer 120, and is configured to determine the thermal property of the sample 102 based on the current value ($I_{1\omega,rms}$), the fundamental voltage value ($V_{1\omega,rms}$), and the third harmonic voltage value ($V_{3\omega,rms}$). In some examples, the processor 122 is further configured to sequentially select the driving frequency from a specified range of driving frequencies. In some examples, the processor 122 can record, at each selected driving frequency, the current value ($I_{1\omega,rms}$), the fundamental voltage value ($V_{1\omega,rms}$), and the third harmonic voltage value ($V_{3\omega,rms}$). In some examples, the processor 122 can, for each selected driving frequency, determine an averaged thermal property profile of the sample from the recorded current value ($I_{1\omega,rms}$), the recorded fundamental voltage value ($V_{1\omega,rms}$), and the recorded third harmonic voltage value ($V_{3\omega,rms}$). In some examples, the processor 122 can determine a spatial thermal property profile of the sample from the averaged thermal property profiles. In some examples, the processor 122 can store the spatial thermal property profile on a computer-readable medium. In some examples, the processor 122 can step sequentially or continuously through a series of frequencies, one at a time. In other examples, the processor 122 can step sequentially or continuously through a series of frequencies, several at a time. In these examples, the processor 122 can select frequencies suitably, so that their third harmonics are easily discernible from the driving frequencies and from one another.

The processor 122 can be a computer system that includes hardware, firmware and software. Examples may also be implemented as instructions stored on a computer-readable storage device, which may be read and executed by at least one processor to perform the operations described herein. A computer-readable storage device may include any non-transitory mechanism for storing information in a form readable by a machine (e.g., a computer). For example, a computer-readable storage device may include read-only memory (ROM), random-access memory (RAM), magnetic disk storage media, optical storage media, flash-memory devices, and other storage devices and media. In some examples, computer systems can include one or more processors, optionally connected to a network, and may be configured with instructions stored on a computer-readable storage device. In one example, processor 122 includes an analog signal processor. In one example, processor 122 includes a look-up table.

In some configurations, the sensing system 100 can include more than one sensor 108. A sensing system 100 having multiple sensors can determine a two- or three-dimensional representation of the thermal property profile in a sample. Each sensor 108 can have its own driver 118 and analyzer 120.

When electrically powered with a periodic signal, the lossy electrical conductor 104 produces a radiated heat pattern that also varies periodically. The periodic heat variations radiate outward, both into the substrate 106 and into the sample 102. The periodic heat variations decay exponentially with respect to distance away from the lossy electrical conductor 104. The scale of the exponential decay is described by a frequency-dependent penetration depth, λ, given by:

$$\lambda = \mathrm{sqrt}(D/\omega),$$

where D is a thermal diffusivity of the substrate 106 and ω is the driving frequency of the lossy electrical conductor 104.

Figure 2:
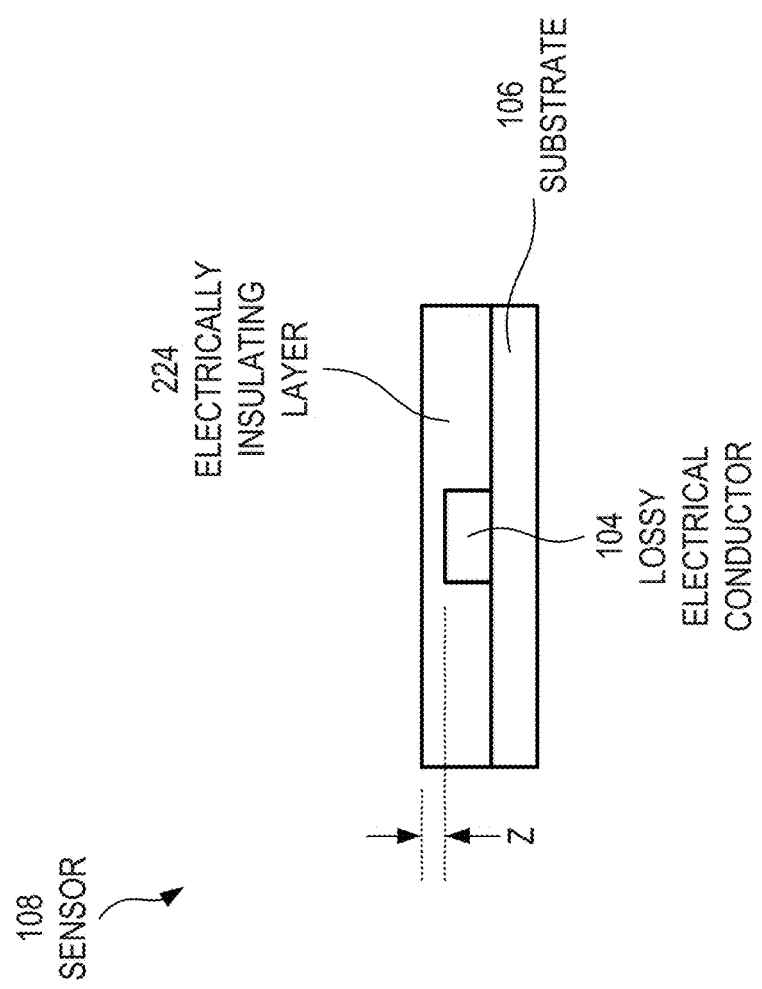
FIG. 2 shows a side-view of an example of a configuration for the sensor of FIG. 1.

FIG. 2 shows a side-view of an example of a configuration for the sensor 108 of FIG. 1. The sensor structure of FIG. 2 is but one example of a suitable sensor structure; other suitable structures can also be used.

The sensor 108 includes a substrate 106, a lossy electrical conductor 104 disposed on the substrate 106, and an electrically insulating layer 224 disposed on the lossy electrical conductor 104. The electrically insulating layer 224 can be deposited on the lossy electrical conductor 104, so that the lossy electrical conductor 104 is disposed between the substrate 106 and the electrically insulating layer 224. Such an electrically insulating layer 224 can insulate the lossy electrical conductor 104, so that contact with an electrically conductive sample 102 (FIG. 1) does not short circuit the lossy electrical conductor 104. The electrically insulating layer 224 can be thick enough to provide electrical insulation, but thin enough so that thermal effects between the lossy electrical conductor 104 and the sample 102 pass easily therethrough. In some examples, the electrically insulating layer 224 has a thickness Z less than the frequency-dependent penetration depth, λ.

Figure 3B:
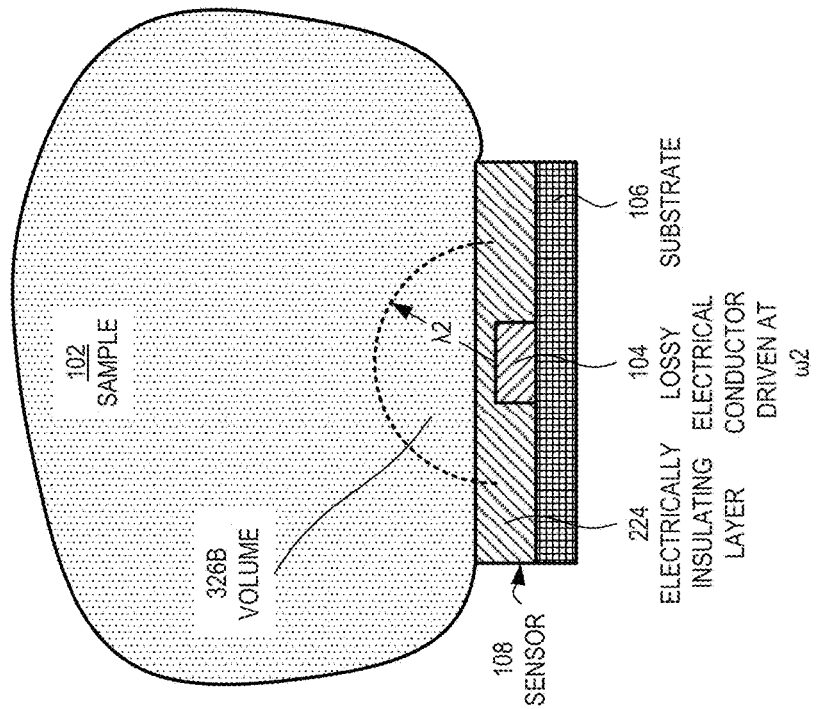
FIGS. 3A-B show side-view cross-sections of an example of a sensor in thermal contact with a sample.
Figure 3A:
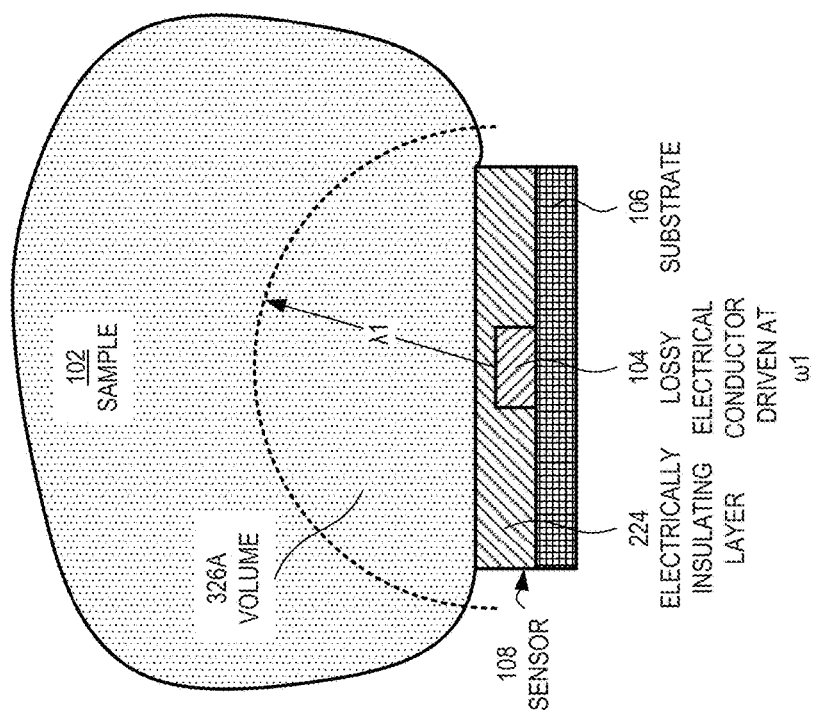

FIGS. 3A and 3B show side-view cross-sections of an example of the sensor 108, in thermal contact with a sample 102.

In FIG. 3A, the lossy electrical conductor 104 is electrically powered at driving frequency ω1. The driving frequency ω1 corresponds to a penetration depth λ1. The penetration depth λ1 corresponds to a volume 326A. For penetration depths significantly larger than length L (FIG. 1) of the lossy electrical conductor 104, the volume 326A can be generally spherical, with a radius of λ1. For penetration depths smaller than L, the shape of the volume 326A can depart from spherical.

A physical interpretation of the volume 326A is that for a driving frequency ω1, the value of a thermal property determined by the three-omega technique is effectively averaged over the volume 326A. In practice, the averaging is not uniform, but is weighted more strongly to points closest to the lossy electrical conductor 104. The weighting decreases at distances away from the lossy electrical conductor 104. At the edge of the volume 326A, the weighting decreases to a specified value, such as $1/e^2$, 1%, or some other suitable value. The weighting does not fall immediately to zero outside the volume 326A, but decreases to a suitably small value at increasing distances away from the lossy electrical conductor 104. In other words, the term averaging, as used herein, is intended to denote a weighted averaging, where the weighting decreases to a specified level at the edge of the volume 326A.

In FIG. 3B, the lossy electrical conductor 104 is electrically powered at driving frequency ω2, where driving frequency ω2 is greater than driving frequency ω1 of FIG. 3A. The driving frequency ω2 corresponds to a penetration depth λ2, which is less than penetration depth ω1 of FIG. 3A. The penetration depth λ2 corresponds to a volume 326B. Volume 326B is smaller than volume 326A. Both volumes 326A and 326B are concentric and extend outward from the lossy electrical conductor 104.

Because the sensing system can vary the driving frequency, the sensing system can therefore vary the penetration depth, and, in turn, vary the volume over which a particular measurement is averaged. As a result, the sensing system can acquire numerous averaged measurements, which are all averaged over differently-sized, concentric volumes that extend outward from the lossy electrical conductor. From these numerous averaged measurements, a processor in the sensing system can perform a fit of thermal property and geometry, and thus obtain a spatial profile of thermal property in the sample. Such fits are well-known to one of ordinary skill in the art. In some examples, a material thermal property is predetermined and a material geometry is determined by the fit. This type of fit can be useful for identifying cracks, anisotropies, defects, or other features in a material environment where the thermal properties are known. In other examples, a material geometry is predetermined and a material thermal property is determined by the fit.

In some examples, a processor determines the plurality of averaged thermal conductivities of the sample, determines the spatial profile of thermal property in the sample, and stores the spatial profile of thermal property on a computer-readable medium.

Figure 4:
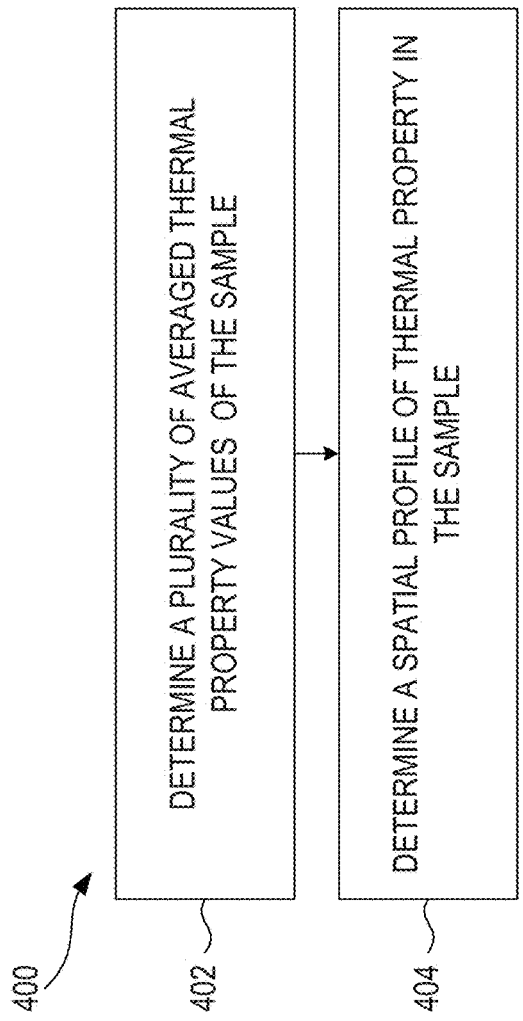
FIG. 4 is a flow chart of an example of a method for determining a spatial profile of thermal property of a sample.

FIG. 4 is a flow chart of an example of a method 400 for determining a spatial profile of thermal property of a sample. The method 400 can be executed by the sensing system 100 of FIG. 1, or by any suitable sensing system. At 402, method 400 determines a plurality of averaged thermal conductivities of the sample. The averaged thermal conductivities are averaged over respective volumes on the sample. The volumes are concentric and differently sized. At 404, method 400 determines a spatial profile of thermal property in the sample based on the plurality of averaged thermal conductivities.

Figure 5:
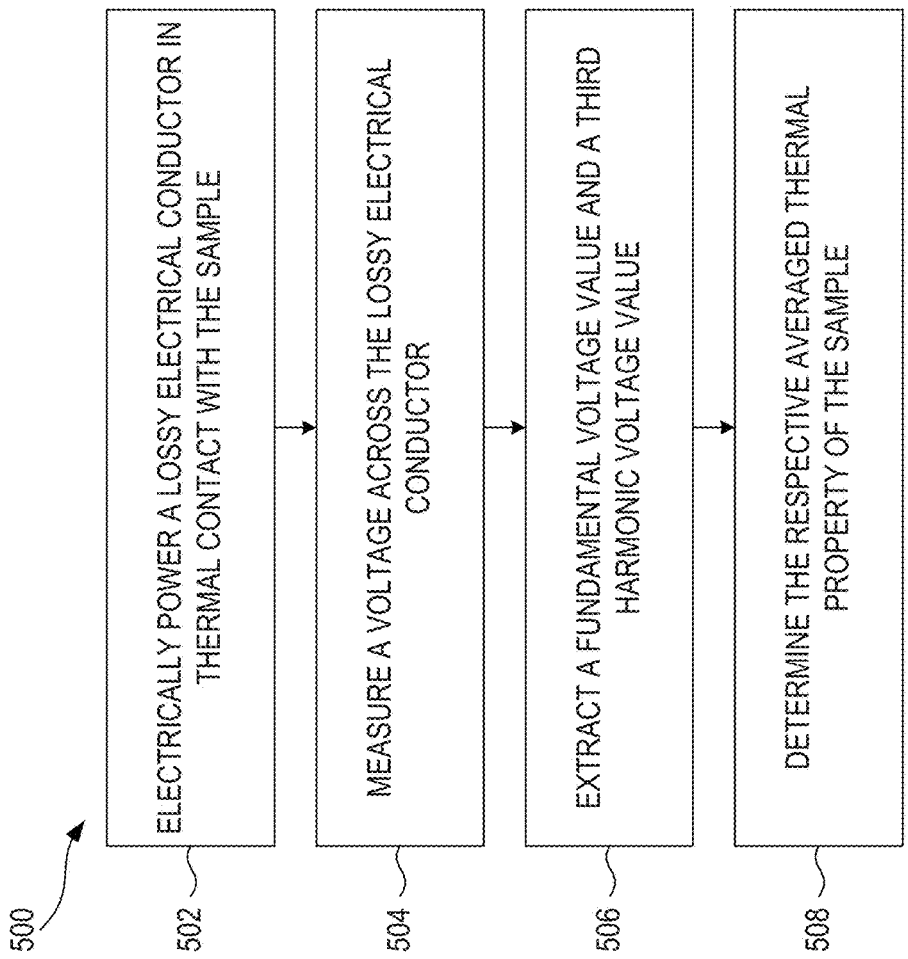
FIG. 5 is a flow chart of an example of a method for determining a plurality of averaged thermal conductivities of the sample, for each averaged thermal property.

FIG. 5 is a flow chart of an example of a method 500 for determining a plurality of averaged thermal conductivities of the sample, for each averaged thermal property. The method 500 can be executed by the sensing system 100 of FIG. 1, or by any suitable sensing system. In some examples, the method 500 corresponds to 402 (FIG. 4). At 502, method 500 electrically powers a lossy electrical conductor in thermal contact with the sample. The lossy electrical conductor is powered at a driving frequency (ω) related to the size of the volume over which the averaged thermal property is averaged. The electrically powered lossy electrical conductor carries a current therethrough. The current has a current value ($I_{1\omega,rms}$) at the respective driving frequency. In some examples, a driver, such as 118 (FIG. 1), provides the electrical power. At 504, method 500 measures a voltage across the lossy electrical conductor. In some examples, an analyzer, such as 120 (FIG. 1), measures the voltage. At 506, method 500 extracts from the measured voltage a fundamental voltage value ($V_{1\omega,rms}$) at the respective driving frequency and a third harmonic voltage value ($V_{3\omega,rms}$) at a third order harmonic of the respective driving frequency. In some examples, an analyzer, such as 120 (FIG. 1), extracts the voltage values. At 508, method 500 determines the respective averaged thermal property of the sample based on the current value ($I_{1\omega,rms}$), the fundamental voltage value ($V_{1\omega,rms}$), and the third harmonic voltage value ($V_{3\omega,rms}$). In some examples, a processor, such as 122 (FIG. 1), determines the respective averaged thermal property.

Three-Omega Method

Accurate knowledge of the thermal conductivities of biological tissues is important for thermal bioengineering, including applications in cryopreservation, cryosurgery, and other thermal therapies. The thermal conductivity of biomaterials is traditionally measured with macroscale techniques such as the steady longitudinal heat flow method or embedded thermistor method. These techniques typically require relatively large, centimeter-scale samples, limiting their applicability to finer biological structures. They are also vulnerable to errors caused by thermal contact resistances and parasitic heat losses. In contrast, the thermal conductivity of inorganic solids such as semiconductor wafers and thin films is commonly measured using the three-omega method. This frequency domain technique is robust against thermal contact resistances and parasitic heat losses. It routinely has sub-millimeter spatial resolution, with theoretical limits down to tens of microns. Here, a three-omega method can be applied for measurements of biological tissues. Thermal conductivity measurements are made on both frozen and un-frozen samples including agar gel, water, and mouse liver, including samples with sub-millimeter thicknesses. The measurement results compare favorably with literature values and span the range from around 0.5 to 2.5 W/m-K. The three-omega technique can be used for thermal measurements of bulk tissues as well as fine sub-millimeter samples.

Thermal therapies are used in several areas of medical treatments. For example, thermal ablation has been used to treat hepatic cancer and has been shown to be superior to other treatment methods, while cryoablation has been used to treat prostate, breast, and renal cancer. In cardiology, cryopreservation of heart valves and blood vessels is used to maintain tissue function for grafts and transplants, and controlled heating and cooling of blood vessels is used to treat atrial fibrillation, peripheral artery disease, and renal hypertension. All of these techniques rely on repeatable and predictable cooling and heating of biological tissues. In the case of ablation, the thermal necrosis volume depends critically on the thermal properties of the tissue. Underestimating the thermal conductivity of local tissues risks creating a larger thermal necrosis volume than intended and damaging nearby healthy and potentially vital tissue, while over-estimation risks failing to kill all cancerous cells leading to a future relapse after treatment. In the case of cryopreservation, controlling the rate of cooling also depends on the thermal properties of the tissue. Cooling too slowly risks dehydrating cells, while cooling too rapidly risks the formation of intracellular ice, both of which can cause undesirable damage or even death to the tissue being preserved.

Several techniques currently exist for measuring the thermal conductivity of biological tissues, such as the guarded hot plate method, the cut bar method, and the embedded thermistor method. However, there are inherent limitations to these techniques. They are susceptible to parasitic heat losses to the environment, thermal contact resistances, and size limitations requiring that samples must be at least approximately one centimeter large in all dimensions in order to be measurable. There are many tissues with characteristic lengths much smaller than 1 cm, such as heart valves (1-2 mm), the pulmonary vein (1-3 mm), the phrenic nerve (<1 mm), the esophagus (1-3 mm), small diameter arteries (1 mm), and fascia (0.1 mm). Any of these tissues could be at risk when thermal therapies are applied to surrounding tissue, and this risk cannot be accurately quantified or controlled until the thermal conductivity of such thin (<5 mm) tissues can be measured.

The three-omega method is a frequency domain electrothermal technique traditionally used to measure the thermal conductivity, k, of inorganic solids such as semiconductor wafers and thin films, and which overcomes all of the above-mentioned difficulties of parasitic heat losses, contact resistances, and small (down to tens of microns) sample sizes. However, the traditional three-omega method has its own limitations. For example, it requires samples to undergo a harsh microfabrication process during which a heater line is deposited on the sample. The heater line can be a lossy electrical conductor, such as 104 (FIG. 1). Such a process involves solvents, vacuum, and temperatures high enough to destroy biological tissues or permanently change their physical properties. Another limitation is the requirement that every sample must have its own dedicated heater line independently and permanently deposited.

In an example of the present subject matter, a device is microfabricated on a substrate. To measure thermal conductivity of a sample, the substrate and device are placed into contact with the sample (or the sample is placed into contact with the substrate and device). After the measurement is taken, the substrate and device can be removed from the sample (or the sample can be removed from the substrate and device). This technique overcomes many limitations of both traditional biological tissue k measurements and the traditional three-omega measurements.

The supported three-omega method can be applied to biological tissues, can measure thin (~1 mm) samples, and can sequentially measure multiple samples in a timely fashion by reusing the same sensor.

In one example of the traditional three-omega method, a small metal heater line with dimensions 65 μm wide by 0.2 μm thick by 2000 μm long (L) is microfabricated directly onto the substrate to be measured, with current and voltage contacts in a four-pad configuration as in FIG. 1. A sinusoidal current $I=I_0 \sin(\omega t)$ is sent through the heater line, with driving angular frequency ω. The electrical resistance of the heater line causes joule heating (also known as resistive heating), which dissipates the electrical energy as heat at a rate proportional to the square of the current, resulting in a constant DC power output plus an AC power output at twice the driving frequency, $Q=Q_0 (1-\cos(2\omega t))$. This causes the temperature of the heater line to oscillate at frequency 2ω. The thermal properties of the substrate determine how large of a temperature gradient is required to transport this heat away from the heater line and into the substrate. Therefore, the magnitude of the heater line's temperature oscillations contains information about the thermal properties of the substrate.

The oscillating temperature gradient results in a thermal wave that propagates radially away from the heater line into the substrate and decays exponentially with increased distance from the heater line. The frequency-dependent penetration depth, $\lambda=\mathrm{sqrt}(D/\omega)$, of the thermal wave is a measure of the characteristic length scale for the exponential attenuation of the amplitude of the thermal wave. D is the thermal diffusivity of the substrate.

The 2ω temperature oscillations of the heater line cause its electrical resistance to oscillate at 2ω, which combines with the 1ω driving current to produce an oscillating voltage with a 3ω frequency component. This 3ω voltage signal, therefore, contains information about the thermal properties of the substrate and can be measured directly using a lock-in amplifier set to monitor the voltage at the third harmonic of the driving frequency. When the portion of this 3ω voltage signal that is in phase with the driving frequency is plotted as a function of the logarithm of the driving frequency, the slope of the resulting line is inversely proportional to the thermal conductivity, k, according to, $$k=[V_{1\omega,rms} I^2_{1\omega,rms}(dR/dT)]/[4\pi L(\partial V_{3\omega,rms}/\partial \ln \{\omega\})],$$

where the equation has been expressed in terms of measurable quantities. V is voltage, I is current, dR/dT is the rate of change of the heater line's electrical resistance with respect to temperature, and subscripts denote harmonics and root-mean-square values.

The $V_{1\omega,rms}$ voltage signal across the heater line combined with the known $I_{1\omega,rms}$ driving current can be used to calculate the average resistance of the heater line, which depends on the heater line's temperature. The heater line can be used as a thermometer to measure the temperature of the sample exactly where the k measurement occurs.

Measurement of thin samples can be achieved by using high frequency driving currents that create short thermal wavelengths, whose penetration depth into the sample is controlled to be much less than the sample's thickness. Because the measurement is transient, operating in the frequency domain, the thermal wavelengths are localized within the sample minimizing the effect of steady-state parasitic heat losses to the environment. Frequencies can be selected to ensure that λ is always at least 5× smaller than the sample thickness in all directions.

Another feature of Eq. (1) is that thermal contact resistances will show up as a constant offset of the in-phase $V_{3\omega,rms}$ versus ln(ω) line, not affecting the slope and hence not affecting the measured value of k. Frequencies can be selected to ensure that λ is always at least 90 μm in the sample, the sensor, and the dielectric layer. Because the 1 μm dielectric layer is much smaller than λ, it appears as a contact resistance and does not affect the slope in Eq. (1).

In one example of the supported three-omega method, a sample is prepared according to the traditional three-omega method, on an amorphous $SiO_2$ substrate (1 mm thick glass). Using standard photolithography and liftoff microfabrication techniques, a gold heater line can be patterned with dimensions 65 μm×0.2 μm×2000 μm, on top of a 5 nm thick chromium adhesion layer. 76 μm diameter bare copper wire can be attached to the four electrodes using conducting silver epoxy.

A 1 μm insulating dielectric layer can be deposited to insulate the heater line and electrical leads from samples that may be electrically conducting. This can be accomplished by dissolving polystyrene pellets in toluene at a concentration of 15 mg/mL. This solution can be dropped directly on top of the area to be insulated, and the surface can be held vertical to allow the excess solution to run off, while the remaining solution can evaporate and leave behind a thin layer of polystyrene. This technique can be tested on glass microscope slides and the repeatable thickness of the coating layer of polystyrene can be verified using a stylus profilometer. The glass substrate, heater line, and dielectric layer assembly is referred to as a sensor, such as 108 (FIG. 2). After the sensor is prepared, samples can be placed directly on top of the heater line to be measured as in FIG. 1.

Each sensor can be characterized by calibrating its thermal conductivity and electrical resistance, both as functions of temperature. First, the resistance can be measured. A 30 mA current at frequency $\omega/2\pi=15$ Hz can be sent through the sensor while the entire structure can be held at a constant temperature, and the $V_{1\omega,rms}$ voltage signal can be recorded. This can be repeated at 5 to 10 different temperatures ranging from approximately −20° C. to 25° C. From this, a plot of resistance ($R=V_{1\omega,rms}/I_{1\omega,rms}$) versus temperature can be obtained, and a slope dR/dT can be extracted from a least-squares linear regression fit.

Figure 6:
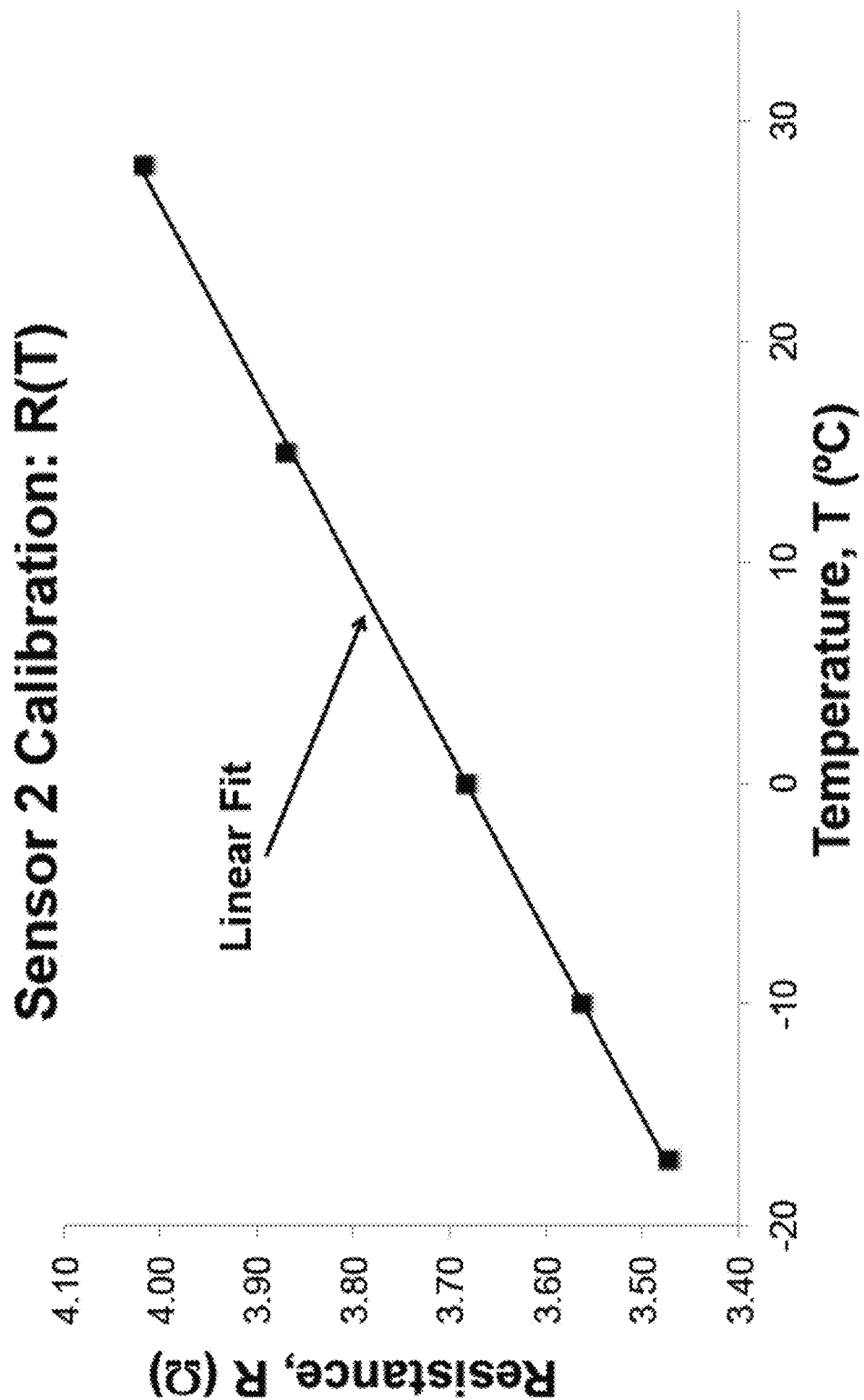
FIG. 6 is a plot of measured resistance of a heater line as a function of temperature.

30 mA allows for strong signal-to-noise ratios, but it can cause non-negligible self-heating of the heater line, of around 3° C. Due to this offset uncertainty in the R(T) curve, another, higher accuracy measurement of the electrical resistance can be performed at room temperature, $T_0=22.9°$ C. This can be done by sweeping the current magnitude and plotting the resistance ($V_{1\omega,rms}/I_{1\omega,rms}$) versus the square of the current. This plot is linear, with the intercept ($R_0$) corresponding to the heater line electrical resistance in the limit of zero joule heating. The sensor temperature can be measured before and after the sweep, and can be found to be the same. Temperature can be measured using a Keithley 2700 multimeter with a K-type thermocouple. Consistent with the known physics of R(T) for gold over the applicable temperature range, it can be assumed that the previously measured slope, dR/dT, is constant, and this slope can be combined with the control point $R_0(T_0)$ to generate a linear function relating the heater line resistance (Ω) to its temperature, as shown in FIG. 6. This function can be used to calculate the temperature of samples based on the measured resistance of the heater line.

Figure 7:
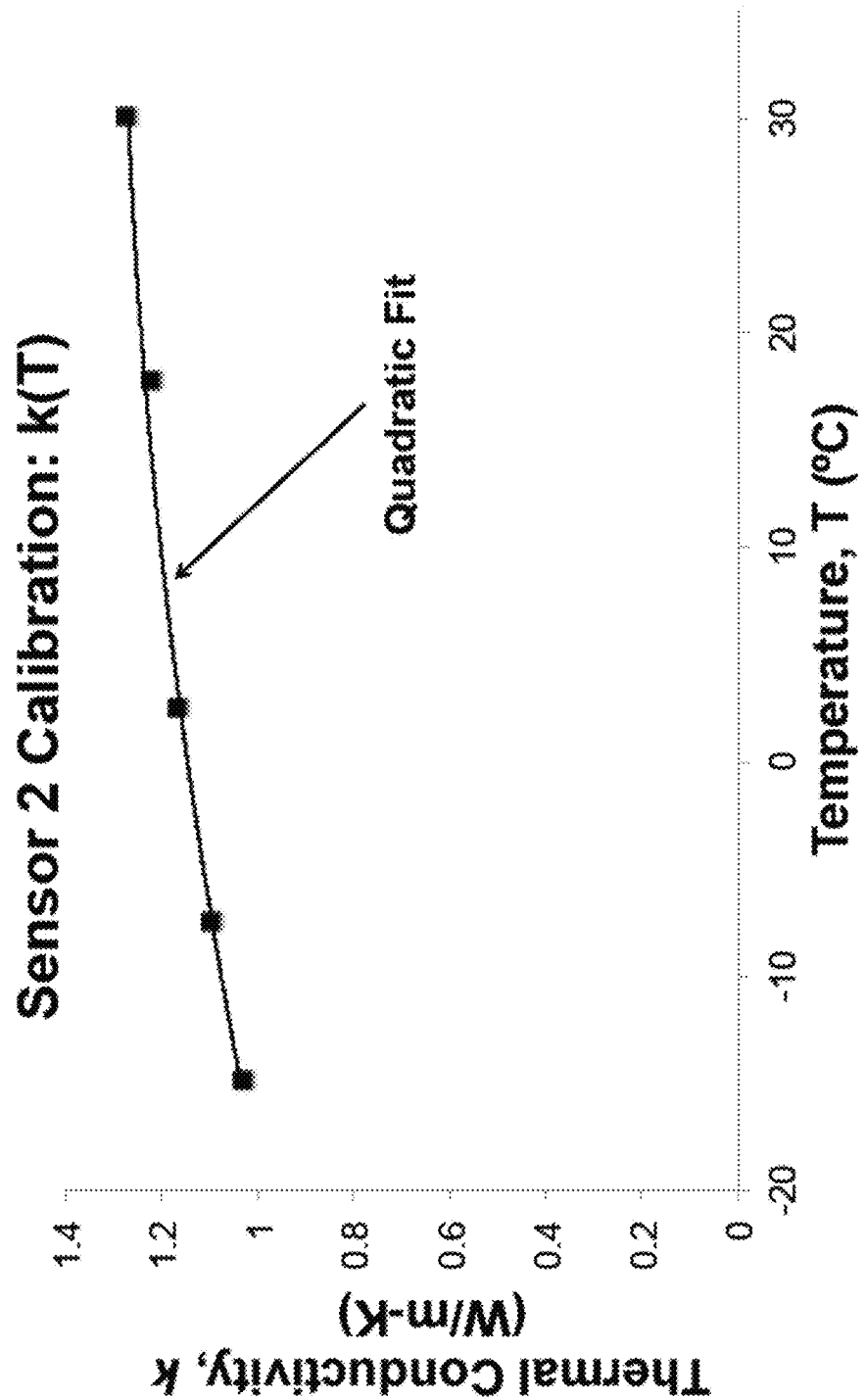
FIG. 7 is a plot of measured thermal property of a sensor as a function of temperature.

After calibrating dR/dT, the thermal conductivity of the sensor can be measured at five temperatures from approximately −15° C. to 30° C., using Eq. (1). A quadratic fit can be applied to the resulting plot to obtain a $k_{sensor}(T)$ function, as illustrated in FIG. 7.

For the traditional three-omega method, Eq. (1) calculates the thermal conductivity based on the rate of heat conduction from the heater line into the substrate below. In the case of the supported three-omega method, heat is conducted out of the heater line into both the substrate below and the sample above. If the sample were made of the same material as the substrate, it would double the heat loss and Eq. (1) would calculate twice the thermal conductivity. In the case when the sample and the sensor both have similar thermal diffusivities (within a factor of 10 of each other), this can be generalized to:

$$k_{measured}=k_{sensor}+k_{sample} \quad (2)$$

neglecting the higher order corrections that make Eq. (2) exact. $k_{measured}$ is the thermal conductivity calculated from applying Eq. (1) directly to the measured quantities, and $k_{sensor}$ is the calibrated k from FIG. 7. For each measurement, $k_{sample}$ can be found by first calculating $k_{measured}$ and then directly subtracting $k_{sensor}$ evaluated at the correct temperature. Equation (2) is the fundamental equation that enables the calculation of samples' thermal conductivities using the supported three-omega method. The heat flux leaving the heater line splits. Part of the heat flux can travel downward into the substrate, while the rest of the heat flux can travel upward through the dielectric film and into the sample. This splitting of the heat can be uneven, and the greater the thermal resistance from the dielectric layer and the dielectric-sample interface, the greater the fraction of total heat directed down into the substrate. The total upper thermal impedance is a series sum of the dielectric layer thermal impedance, contact resistance, and the sample thermal impedance. This combines in parallel with the lower substrate thermal impedance.

The majority of the error of using Eq. (2) is due to the mismatch between the sample and substrate's thermal diffusivities. For a particular heater line geometry, for samples having a D within an order of magnitude of $5\times10^{-6}$ m$^2$/sec, and for frequency ranges≤20 Hz, there can be a maximum total error of 3% in Eq. (2) as compared to the exact solution. Particular measurements can exhibit a maximum error of no more than 2% from Eq. (2), and thus the corrections can be left out of the calculations below.

The thermal flux directly from the sample to the substrate, laterally outside the footprint area of the heater line, can be neglected in favor of the boundary mismatch model, which is a reasonable assumption when the thermal diffusivities are similar.

All samples can be unfrozen and very hydrated when originally placed on the sensor and therefore can be assumed to be in intimate thermal contact with the dielectric layer. Accordingly, order of magnitude values for the thermal conductance at this interface directly above the heater line can be used to quantify its effect. The combination of this contact thermal resistance with the thermal impedance of the dielectric layer itself can be found to contribute cumulatively negligible error toward the determination of $k_{sample}$ (at most 0.2% error but usually less than 0.02%) and can also be left out of the calculations below.

The sensor can be mounted on top of a Peltier module for temperature control with a thin layer of Omegatherm 201 thermal paste. The sensor-Peltier sandwich can be housed inside an aluminum cavity with lid (wall thicknesses 1 cm) to shield against outside electrical noise and to reduce moisture evaporation from the sample. Metal spring clips can clamp the sensor to the Peltier module and in turn to the cavity floor. A small hole in the cavity housing can allow access to electrical leads while padding helping mechanically anchor these wires. For subzero measurements, the entire system can be placed inside a commercial freezer. The freezer's rate of temperature drift due to cycling can be measured to be no more than 0.25° C./minute, whereas the temperature controller can correct temperature on the order of 1° C./second, ensuring the sample's temperature can be held constant. This setup can be favorable over a Peltier-cooled sample in room temperature setup, because putting the entire housing in a freezer minimizes thermal gradients within the aluminum housing cavity, decreasing uncertainty in the temperature of the finite thickness sample. For suprazero measurements, the housing can be placed in ambient atmosphere at room temperature. For all measurements, the temperature of the sample, the internal temperature of the freezer, and the ambient room temperature can be recorded continuously throughout the experiment.

Samples can be carefully placed directly on the heater line of the sensor, ensuring the sample extended laterally at least 0.5 mm around the perimeter of the heater line in all directions as in FIG. 1. Samples can be held in place by their own weight without clamping. Because all samples can be soft, clamping them in place can risk creating asymmetric pressures and altering their physical properties. No samples shifted position during measurement. All frozen samples (including ice) can be initially placed on the heater line in their thawed form, which can conform to the surface of the sensor and heater line, and are then frozen in place. All samples can be also carefully peeled off and inspected after each measurement to look for signs of trapped pockets of air, incomplete or non-uniform contact, or significant geometry changes during the experiment. These conditions are not reflected in the data presented here.

Consider next, the preparation of each of the three different types of samples measured: ice, agar gel, and mouse liver. Deionized water can be used for ice measurements. Water can be boiled for 5 minutes prior to freezing. Placing a 30 μL bead of water on the heater line and then flash-freezing it from below using the Peltier module can minimize internally trapped air bubbles, especially near the bottom close to the heater line. Agar gel can be prepared by dissolving agarose powder in tap water preheated to approximately 65° C. The solution can contain 0.5% agar gel by weight. The heated solution can be stirred for 20 minutes until clear and colorless, and then can be allowed to set in a refrigerator overnight.

Fresh mouse liver, stored in phosphate buffered saline, can be used as the biological tissue to be measured. Thin samples can be prepared by placing the bulk tissue in a recessed surface constructed from 1 mm thick microscope slides, while a microtome blade can be used to slice across the top of the recession. All liver measurements can be done within 3 days of receiving the fresh tissue, which can be stored in the refrigerator in phosphate buffered saline when not being handled.

All thawed samples can be covered with a layer of plastic wrap to minimize evaporative losses from the sample during the measurement. First, the samples can be placed on the heater line, then a small square of plastic wrap can be placed directly on top, large enough to cover both the sample and the sensor, and can be gently pressed down to fit the shape of the sample. Small quantities of water (for agar gel) or phosphate buffered saline (for liver) can be injected between the plastic wrap and the sample to expel trapped air bubbles if necessary.

Figure 8:
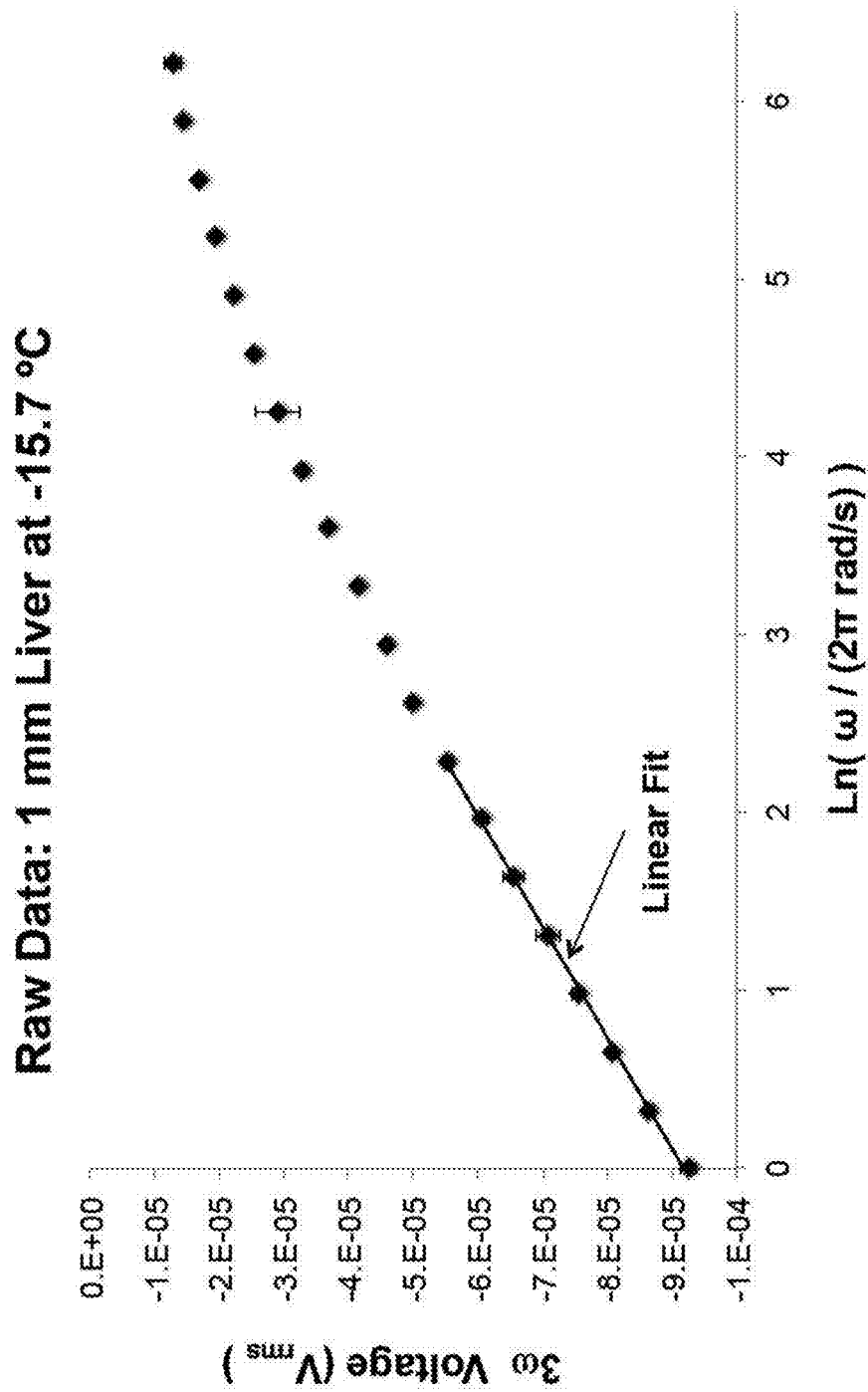
FIG. 8 is a plot of third harmonic voltage value as a function of a natural log of the fundamental driving frequency.

A representative set of raw three-omega data for 1 mm liver tissue at −15.7° C. is plotted in FIG. 8. The low frequency portion of the curve can be used to calculate k. All thermal conductivities can be calculated from within the frequency range 1 Hz<ω/2π<20 Hz, due to physical limitations. In the low frequency limit, λ can approach the thickness of the sample or sensor's substrate. In the high frequency limit, λ can approach the width of the heater line. Both of these limits can violate the analytical model used in deriving Eq. (1). These upper and lower bounds on ω can agree with the raw data plots and with which frequency intervals are linear. The results can be summarized in FIGS. 9-12.

Figure 9:
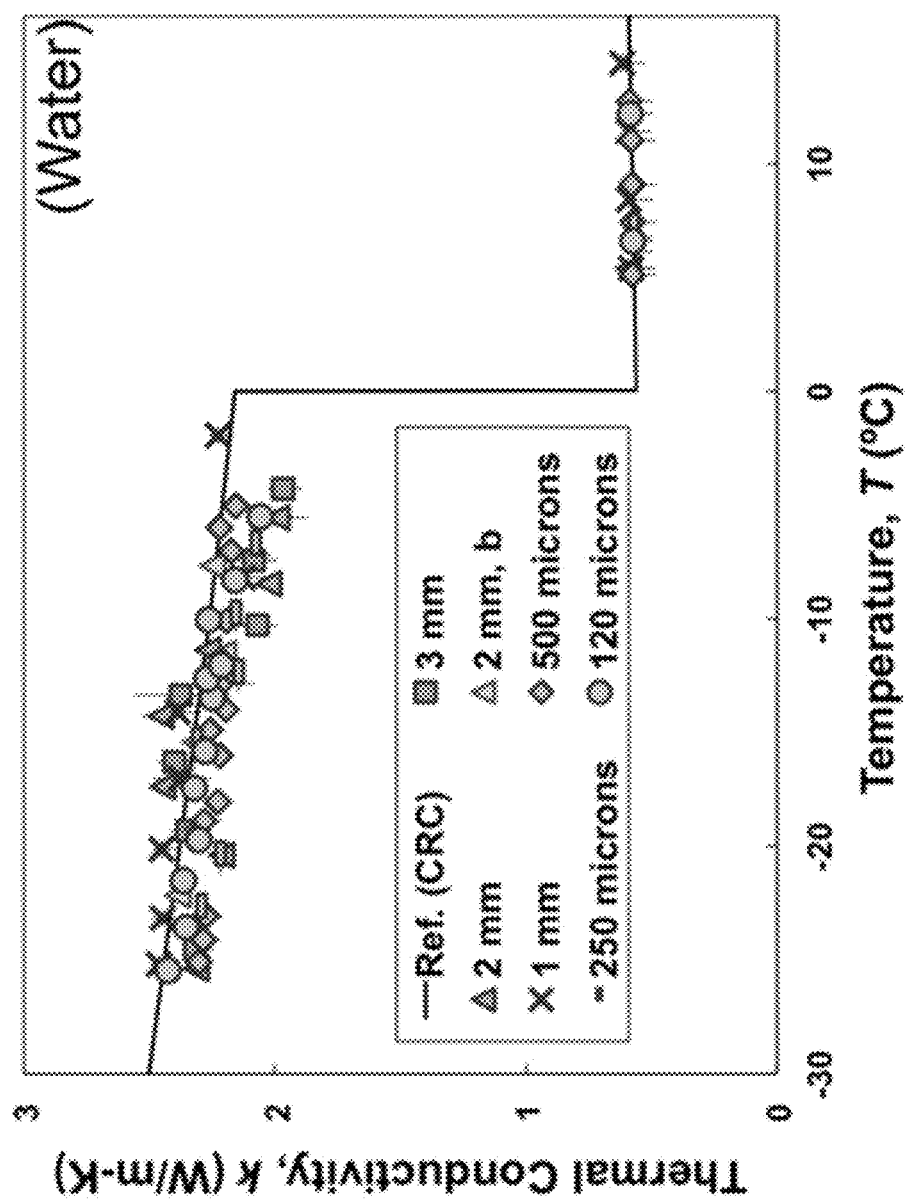
FIG. 9 shows thermal conductivity versus temperature for ice and water.

FIG. 9 shows thermal conductivity (k) versus temperature (T) for ice and water. The data points are experimental measurements. Different sample thicknesses are shown with different marker shapes. Different sensors are shown with different marker shades. The solid line is a reference curve showing an accepted literature value of thermal conductivity. The reference curve was published in *The CRC Handbook of Chemistry and Physics*, 90th Edition (CRC Press, 2009). Error bars (standard deviation) represent the combined effects of measurement uncertainty and estimated modeling error. In most cases, the error bars are smaller than the size of the plotted points. These data are obtained using 2 sensors and 10 samples. These results confirm very good accuracy for both ice (<5% error) and water (<2% for water) as compared to the accepted literature values.

Figure 10:
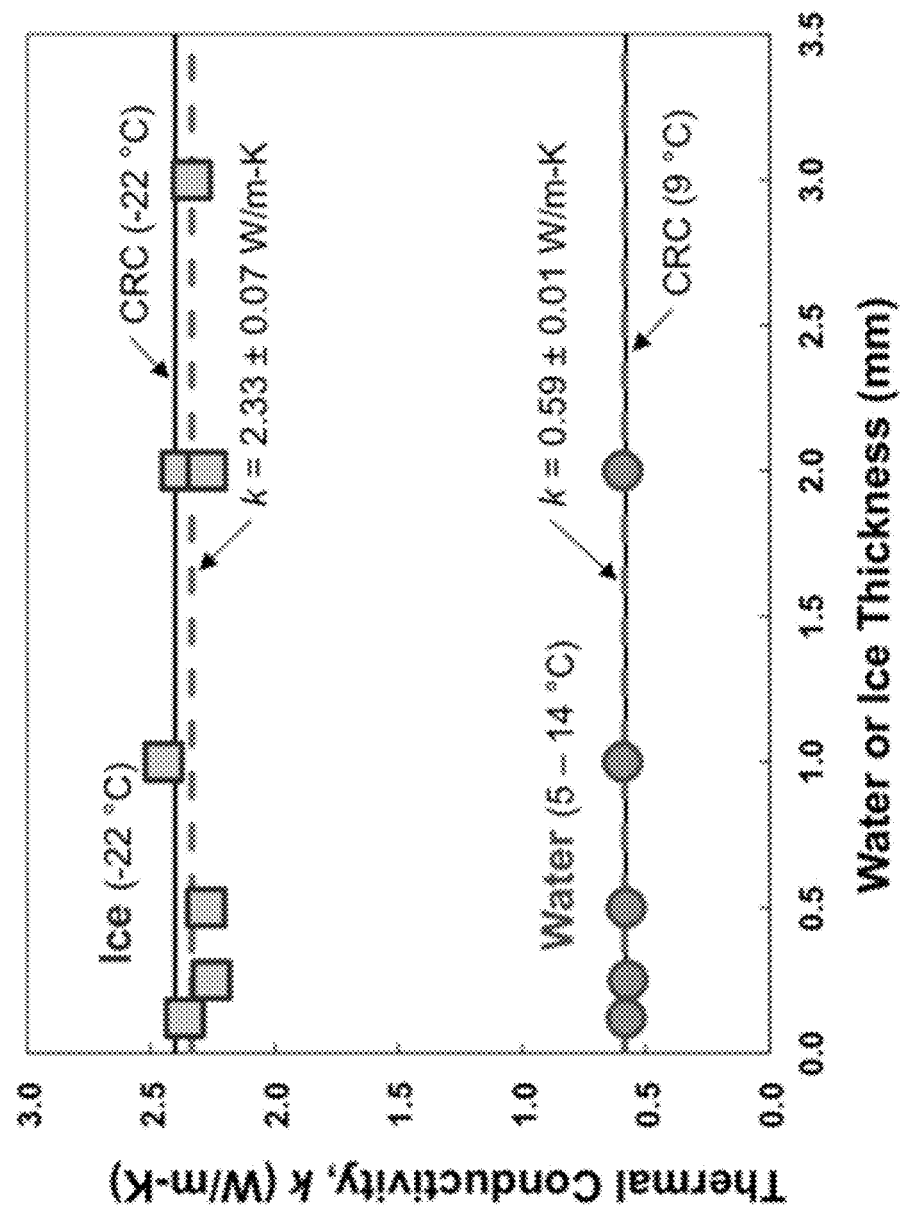
FIG. 10 shows a subset of the data from FIG. 9, interpolated to −22° C. for ice and averaged over all temperatures for water.

FIG. 10 shows a subset of the data from FIG. 9, interpolated to −22° C. for ice and averaged over all temperatures for water. Each point represents a unique sample. No trend with sample thickness is observed. Dashed lines indicate average thermal conductivity with the listed value, and black lines are CRC literature reference data.

The plots of FIGS. 9 and 10 demonstrate the precision, accuracy, and reusability of the bi-directional three-omega sensors, as well as their ability to measure a wide range of sample thicknesses. The data in FIGS. 9 and 10 use a range of sample thickness from 0.1 mm to 3 mm, and it is expected that this measurement technique can be also applied to samples outside this range.

FIG. 11A shows thermal conductivity (k) versus temperature (T) for mouse liver. FIG. 11B shows a close-up of data points from the rightmost edge of the plot in FIG. 11A. The data points are experimental measurements. Different sample thicknesses are shown with different marker shapes. Different sensors are shown with different marker shades. Reference liver data (empty circles) are from the literature and include data from pig, cow, human, dog, and rabbit livers, all more than 10 mm thick. Data represent 16 samples measured using 6 sensors in two different laboratories. The solid line shows the accepted literature value of thermal conductivity for water (not mouse liver), from FIG. 9. Error bars (standard deviation) represent the combined effects of measurement uncertainty and estimated modeling error.

Figure 12:
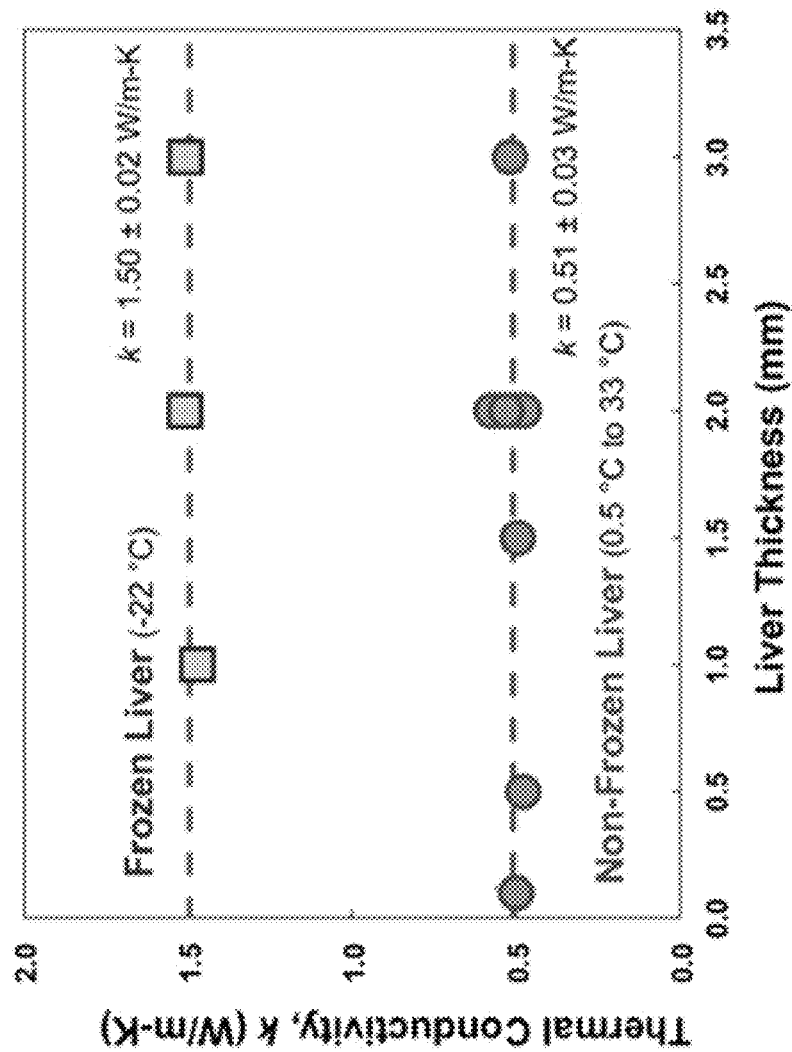
FIG. 12 shows a subset of the data from FIG. 11A-B, interpolated where possible to −22° C. for frozen liver, and averaged over all temperatures for non-frozen liver.

FIG. 12 shows a subset of the data from FIG. 11A-B, interpolated where possible to −22° C. for frozen liver, and averaged over all temperatures for non-frozen liver. Each point represents one sample. No trend with sample thickness is observed. Dashed lines indicate average thermal conductivity. The data in FIGS. 11A-B and 12 use a range of sample thickness from 0.1 mm to 3 mm, and it is expected that this measurement technique can be also applied to samples outside this range.

In summary, the three-omega technique discussed herein can be used for biological tissue thermal conductivity measurements. This is an adaptation of the traditional three-omega technique with the heater line fabricated onto a separately characterized substrate creating a sensor that can be repeatedly used to measure multiple samples in quick succession. This technique utilizes advantages of the traditional three-omega technique—ability to measure thin samples, and negligible error due to parasitic heat losses or thermal contact resistances—and applies it to biological tissues and other soft and hydrated samples otherwise inaccessible to three-omega methods.

The above Detailed Description includes references to the accompanying drawings, which form a part of the Detailed Description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, assembly, device, kit, article, or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The claimed invention is:

1. A sensing system for determining a thermal conductivity of a sample, the sensing system comprising:
a lossy electrical conductor configured to thermally contact the sample;
a driver configured to electrically power the lossy electrical conductor at a driving frequency, the electrically powered lossy electrical conductor configured to carry a current therethrough, the current having a current value at the driving frequency;
an analyzer configured to measure a voltage across the lossy electrical conductor and extract from the measured voltage a fundamental voltage value at the driving frequency and a third harmonic voltage value at a third order harmonic of the driving frequency; and
a processor coupled to the driver and the analyzer and configured to determine the thermal conductivity of the sample based on the current value, the fundamental voltage value, and the third harmonic voltage value.

2. The sensing system of claim 1, wherein the processor is further configured to sequentially select the driving frequency from a specified range of driving frequencies.

3. The sensing system of claim 2, wherein the processor is further configured to record, at each selected driving frequency, the current value, the fundamental voltage value, and the third harmonic voltage value.

4. The sensing system of claim 3, wherein the processor is further configured to, for each selected driving frequency, determine an averaged thermal conductivity profile of the sample from the recorded current value, the recorded fundamental voltage value, and the recorded third harmonic voltage value.

5. The sensing system of claim 4, wherein the processor is further configured to determine a spatial thermal conductivity profile of the sample from the averaged thermal conductivity profiles.

6. The sensing system of claim 1, wherein the analyzer comprises at least one lock-in amplifier configured to extract the fundamental voltage value and the third harmonic voltage value from the measured voltage.

7. The sensing system of claim 1, wherein the analyzer performs a Fast Fourier Transform on the measured voltage to extract the fundamental voltage value and the third harmonic voltage value from the measured voltage.

8. The sensing system of claim 1, wherein the driver provides a trigger signal to the analyzer at the driving frequency.

9. The sensing system of claim 1,
wherein the lossy electrical conductor has a length, L;
wherein the lossy electrical conductor has a characteristic rate of change of resistance with respect to temperature, dR/dT; and
wherein the processor determines a measured thermal conductivity, $k_{measured}$, from:

$$k_{measured}=[V_{1\omega,rms}I^2_{1\omega,rms}(dR/dT)]/[4\pi L(\partial V_{3\omega,rms}/\partial \ln\{\omega\})],$$

where $\omega$ is the driving frequency, $I_{1\omega,rms}$ is the current value, $V_{1\omega,rms}$ is the fundamental voltage value, and $V_{3\omega,rms}$ is the third harmonic voltage value.

10. The sensing system of claim 9, wherein the lossy electrical conductor is deposited on a substrate;
wherein the lossy electrical conductor and substrate form a sensor having a characteristic thermal conductivity, $k_{sensor}$;
wherein the processor determines the thermal conductivity of the sample, $k_{sample}$, from:

$$k_{sample}=k_{measured}-k_{sensor}.$$

11. The sensing system of claim 10, wherein the sensor further comprises an electrically insulating layer deposited on the lossy electrical conductor, the electrically insulating layer having a thermal diffusivity, D, the electrically insulating layer having a thickness less than a frequency-dependent penetration depth, the penetration depth, k, being given by:

$$\lambda=\mathrm{sqrt}(D/\omega).$$

12. A sensing system for determining a spatial thermal conductivity profile of a sample, the sensing system comprising:
- a lossy electrical conductor configured to contact the sample;
- a processor configured to select driving frequencies from a selected range of driving frequencies, each selected driving frequency having an associated penetration depth in the sample, each penetration depth corresponding to a respective volume in the sample, the volumes being concentric and extending outward from the lossy electrical conductor;
- a driver configured to, for each selected driving frequency, receive the selected driving frequency and electrically power the lossy electrical conductor at the selected driving frequency, the electrically powered lossy electrical conductor configured to carry a current therethrough, the current having a current value at the selected driving frequency;
- an analyzer configured to, for each selected driving frequency, measure a voltage across the lossy electrical conductor and extract from the measured voltage a fundamental voltage value at the selected driving frequency and a third harmonic voltage value at a third order harmonic of the selected driving frequency;
- the processor being further configured to determine, for each selected driving frequency, an averaged thermal conductivity of the sample based on the corresponding current value, the corresponding fundamental voltage value, and the corresponding third harmonic voltage value,
- whereby, for each selected driving frequency, the averaged thermal conductivity is averaged over the corresponding volume in the sample.

13. The sensing system of claim 12, wherein the processor is further configured to form a spatial thermal conductivity profile of the sample, based on the averaged thermal conductivities of the sample.

14. The sensing system of claim 12, wherein the processor is configured to sequentially select the driving frequencies from the selected range of driving frequencies.

15. The sensing system of claim 12, wherein the processor is configured to select a plurality of driving frequencies from the selected range of driving frequencies.

* * * * *

UNITED STATES PATENT AND TRADEMARK OFFICE
CERTIFICATE OF CORRECTION

| | |
|---|---|
| PATENT NO. | : 9,851,316 B2 |
| APPLICATION NO. | : 14/533510 |
| DATED | : December 26, 2017 |
| INVENTOR(S) | : Lubner et al. |

Page 1 of 2

It is certified that error appears in the above-identified patent and that said Letters Patent is hereby corrected as shown below:

On the Title Page

In Column 2, under item (56) "Other Publications", Line 2, delete "3w" and insert --$3\omega$-- therefor In Column 2, under item (56) "Other Publications", Line 2, delete "APplied" and insert --Applied-- therefor On page 2, in Column 1, under item (56) "Other Publications", Line 2, delete "techniquess" and insert --techniques-- therefor On page 2, in Column 1, under item (56) "Other Publications", Line 5, after "Cryoablation", delete "Treatment of" and insert --of the-- therefor On page 2, in Column 1, under item (56) "Other Publications", Lines 27-28, delete "measurement" and insert --measurements-- therefor On page 2, in Column 1, under item (56) "Other Publications", Line 31, delete "Tisse" and insert --Tissue-- therefor On page 2, in Column 1, under item (56) "Other Publications", Line 35, after "Technique", insert --for--

On page 2, in Column 1, under item (56) "Other Publications", Line 38, delete ""1•, 2•, and 3•" and insert --"$1\omega$, $2\omega$, and $3\omega$-- therefor On page 2, in Column 2, under item (56) "Other Publications", Line 60, delete "233-313° K" and insert --233-313K-- therefor Signed and Sealed this
Eleventh Day of January, 2022

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 9,851,316 B2

In the Specification

In Column 4, Line 16, after "from", delete "FIG." and insert --FIGS.-- therefor

In Column 14, Line 47, after "from", delete "FIG." and insert --FIGS.-- therefor In the Claims In Column 16, Lines 44-45, in Claim 9, delete "$k_{measured} = [V_{1\omega,rms} I^2_{1\omega,rms}(dR/dT)]/[4\pi L(\partial V_{3m,rms}/\partial \ln\{\omega\})],$" and insert --$k_{measured}=[V_{1\omega,rms}I^2_{1\omega,rms}(dR/dT)]/[4\pi L(\partial V_{3\omega,rms}/\partial \ln\{\omega\})],$-- therefor In Column 16, Line 64, in Claim 11, delete "k," and insert --λ,-- therefor